United States Patent
Fuhr et al.

(10) Patent No.: US 7,984,616 B2
(45) Date of Patent: Jul. 26, 2011

(54) LOW-TEMPERATURE STORAGE OF SUSPENSION SAMPLES IN SUSPENDED SAMPLE CHAMBERS

(75) Inventors: Günter Fuhr, Berlin (DE); Heiko Zimmermann, Saarbrücken (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 939 days.

(21) Appl. No.: 10/532,017

(22) Filed: Apr. 20, 2005

(65) Prior Publication Data

US 2006/0014134 A1   Jan. 19, 2006

Related U.S. Application Data

(63) Continuation of application No. PCT/EP03/12355, filed on Nov. 5, 2003.

(30) Foreign Application Priority Data

Nov. 6, 2002   (DE) .................................. 102 51 668

(51) Int. Cl.
*F25D 25/00*   (2006.01)

(52) U.S. Cl. ............................................. 62/62; 62/64
(58) Field of Classification Search ................ 62/62, 63, 62/64, 65, 78, 135; 435/183, 284.1, 260, 435/286.1, 304.1, 307.1; 422/99, 100, 101, 422/102, 103, 104
See application file for complete search history.

(56) References Cited

U.S. PATENT DOCUMENTS

| 1,779,174 | A | * | 10/1930 | Larsen ............................ 294/65 |
| 3,292,424 | A | * | 12/1966 | Smollett et al. ............... 73/61.41 |
| 3,344,406 | A | * | 9/1967 | Vinal ............................. 711/100 |
| 4,182,739 | A | * | 1/1980 | Curtis ............................. 422/47 |
| 4,262,494 | A |   | 4/1981 | Karow, Jr. |
| 4,618,586 | A | * | 10/1986 | Walker ....................... 435/286.5 |
| 4,739,622 | A | * | 4/1988 | Smith .............................. 62/78 |
| 5,064,764 | A | * | 11/1991 | Besnainon et al. ......... 435/297.4 |
| 5,390,553 | A |   | 2/1995 | Lynn |
| 5,510,262 | A | * | 4/1996 | Stephanopoulos et al. ... 435/403 |
| 5,827,480 | A | * | 10/1998 | Haff et al. .................... 422/68.1 |
| 5,863,715 | A |   | 1/1999 | Rajotte et al. |
| 5,925,511 | A |   | 7/1999 | Fuhr et al. |
| 6,273,298 | B1 |  | 8/2001 | Post |

(Continued)

FOREIGN PATENT DOCUMENTS

DE   19736470 C2   3/1999

(Continued)

OTHER PUBLICATIONS

Abstract of JP 7-280714 A to Suzuki et al.*

*Primary Examiner* — Mohammad Ali
(74) *Attorney, Agent, or Firm* — Caesar, Rivise, Bernstein, Cohen & Pokotilow, Ltd.

(57) ABSTRACT

A cryostorage device (100) is described that includes at least one data storage device (200) and at least one sample receptacle device (300) with at least one sample chamber (301, 302, etc.) for the uptake of a suspension sample, the at least one sample chamber (301, 302, etc.) being connected to the data storage device (200) and having a elongated, hollow shape that extends from an inlet end (320) over a predetermined length to an outlet end (330) and being attached to the at least one data storage device (200) in a flexible and movably hanging manner.

26 Claims, 7 Drawing Sheets

U.S. PATENT DOCUMENTS

| | | | |
|---|---|---|---|
| 6,479,301 B1 * | 11/2002 | Balch et al. | 506/16 |
| 6,646,238 B1 | 11/2003 | Fuhr et al. | |
| 6,698,212 B2 * | 3/2004 | Viegas et al. | 62/50.2 |
| 6,811,750 B2 * | 11/2004 | Patterson et al. | 422/45 |
| RE39,449 E * | 12/2006 | Pages | 422/101 |
| 2002/0007256 A1 * | 1/2002 | Takiue | 702/188 |
| 2002/0164824 A1 * | 11/2002 | Xiao et al. | 436/524 |
| 2003/0076203 A1 * | 4/2003 | Brooks | 335/128 |

FOREIGN PATENT DOCUMENTS

| | | |
|---|---|---|
| DE | 19841554 A1 | 3/2000 |
| DE | 19921236 A1 | 11/2000 |
| EP | 0804073 B1 | 11/1997 |
| JP | 7-280714 A * | 10/1995 |
| WO | WO 99/10763 A1 | 3/1999 |
| WO | WO 99/20104 A1 | 4/1999 |
| WO | WO 02/46719 A2 | 6/2002 |

* cited by examiner

LOW-TEMPERATURE STORAGE OF SUSPENSION SAMPLES IN SUSPENDED SAMPLE CHAMBERS

BACKGROUND OF THE INVENTION

The invention relates to devices for the low-temperature storage (in particular cryostorage, cryopreservation) of suspension samples, in particular a cryostorage device for suspended biological cells, cell groups, or cell components, and methods for low-temperature storage.

The cryostorage of biological samples has numerous applications that are aimed at a continuous storing of the samples while maintaining their vitality state. The devices used for cryostorage are adapted to the particular samples and the requirements during sample handling. In transplantation medicine, for example, organs or organ parts may be stored at low temperatures. In transfusion medicine, blood donations are stored in the deep-frozen state in blood banks.

In conventional applications of cryostorage, frequently the point is to accommodate the largest possible sample volumes in the narrowest possible space. For example, blood donations are kept in blood bags or blood tubes that may be densely packed in the blood bank. The blood bags are provided with a labeling (e.g. bar code) in order to allow for a selective and error-free removal from the blood bank. This conventional cryostorage is limited to use with large samples (ml to l range). However, in cell biology and in molecular biotechnology, the task exists to store and, if necessary, process biological samples of minimal size (single cells, cell groups, or cell components) in the deep frozen state.

In EP 804 073, for example, the cryoprocessing of individual cells is described. Cells are fixed on a substrate in the deep frozen state, stored and, if necessary, processed. This technique has the disadvantage that the storing of the cells that are fixed on substrates may be relatively space-consuming, so that the assembly of a cryo cell bank is complicated. Furthermore, in order to avoid contaminations of cryo-fixed cells, the substrates that are loaded with the samples have to be provided with a protective layer. The handling of the samples stored in such a manner is thereby complicated.

It is described in DE 199 21 236 to deposit drop-shaped suspension samples for cryopreservation on structured substrates, with the help of which the handleability of the frozen samples is facilitated. As carriers of the samples the substrates possess sample receptacles in the form of recesses, the size of which is adapted to the drop volume. The structured substrates may feature matrix-like arranged sample receptacles, as known from micro- or nanotiter plates. Theses cryo-substrates have disadvantages with respect to sample loading and sample withdrawal. For sample loading, all sample receptacles have to be filled by means of a dispensing device. This can be very time-consuming with use of single dispensers. When a multiplicity of parallel working dispensers is used, their geometric arrangement has to be adapted to the cryo-substrate. For sample withdrawal, the drop that is stored in a sample receptacle has to be completely thawed, even if only a part of the drop is needed.

In U.S. Pat. No. 4,262,494, a cryostorage device with a plurality of capillary sample chambers that are arranged in a portable cooling container is described. The sample chambers are arranged protruding from a wall of the cooling container with spacing between them. This cryostorage device is optimized specifically for the transport of cryo-samples. It has disadvantages with respect to the loading of the rigidly formed sample chambers and the long-term storage under cryo-conditions.

A cryostorage device with at least one tubular or pillow-shaped sample chamber that is attached to a data storage is known from WO 02/46719. The attachment is made directly or with a holding frame on an encapsulation of the data storage. With this technique it may be disadvantageous that an auxiliary device may be required for loading of the sample chamber. In addition, the size and thereby the load capacity of the sample chamber is limited by the dimensioning of the data storage. Capillary sample chambers for cryostorage are also described in WO 99/20104. The sample chambers are embedded in a cooling body, which results in the same disadvantages as with the technique according to WO 02/46719.

It is the object of the invention to provide an improved cryostorage device, with the help of which the disadvantages of conventional cryostorage devices are overcome and which in particular allows for a simplified loading with a multiplicity of suspended cells, cell groups, or cell components within short periods of time and which allows for a selective, partial withdrawal of sample components. In particular, the cryostorage device should also allow for the recording and reading of data that belong to each stored sample. It is also the object of the invention to provide an improved method for cryostorage.

SUMMARY OF THE INVENTION

The basic idea of the invention is to advance a generic cryostorage device with at least one data storage device and at least one long-stretched sample chamber to that effect, that the at least one sample chamber is attached to the at least one data storage device in a flexible and movably hanging manner. Through this measure, a number of advantages are achieved that benefit the sample loading, the monitoring of the cryo-stored state, and the withdrawal of samples. Thus, sample chambers used according to the invention may be quickly filled or emptied. The sample chambers are miniturizable and may be flexibly adapted to the conditions of use. The inlet ends of a multiplicity of simultaneously used sample chambers may be adapted to any arrangement of sample reservoirs, from which samples are to be withdrawn, without problems. The sample chambers allow for a sealing of the samples against the environment. Contamination from the surrounding gaseous or liquid phase (e.g., from a cooling medium) is eliminated. From a sample chamber provided according to the invention, samples may be withdrawn through thawing of the entire sample chamber, or partial samples may be withdrawn through mechanical separation without the entire sample chamber being thawed. The mechanical separation may even take place as a result of local heating, without a loss of the sample provided in the remainder of the sample chamber occurring.

On the data storage device are preferably attached a multiplicity of long-stretched sample chambers, in particular a multiplicity of tubes or capillaries that in the loaded state may be immersed hanging in a gaseous or liquid cooling medium. The elongated sample chambers may be formed with a length that is freely selected according to the concrete conditions (in particular amount of sample, size of the cryo-container, etc.). Unlike conventional techniques, larger amounts of sample may be preserved.

In accordance with a preferred embodiment of the invention, the sample chamber possesses a cross-sectional dimension, in particular of the inlet and outlet ends, that is essentially smaller than the length of the sample chamber, so that the shape of a hollow cylinder, hollow cone, pipe, tube, hollow needle, or capillary is the result. This embodiment may have advantages with respect to the loading of the sample chamber. Liquid transport in the sample chamber may occur as a result of capillary forces or external positive or negative pressure.

The at least one sample chamber preferably consists of an inherently flexible, bendable material. First of all, this allows for a loading in a space-saving way. The sample chambers can be loaded for example in the laboratory or in a medical practice even with large length in a wound-up state. The bendability of the material further allows for the positioning in a flexible and movably hanging manner on the at least one data storage device through a direct attachment of the sample chamber to the data storage device. This has the advantage of a compact architecture. Alternatively, an attachment device may be provided, with the help of which the at least one sample chamber is attached to the data storage device in a flexible and movably hanging manner. Thereby, the mechanical separation of individual sample chambers from the cryostorage device, in particular in the cooled state, may be simplified. The attachment device comprises for example flexible strips or bands that are arranged individually or as a bundle, each with a sample chamber attached to one end and the other end attached to the data storage device.

In accordance with another preferred embodiment of the invention, the data storage device may comprise at least one data storage (e.g. a memory chip) with a housing, to which the at least one sample chamber is connected, if necessary via the attachment device. The housing advantageously allows for the use of different data storages, so that the flexibility in using the cryostorage device is improved.

In accordance with another advantageous embodiment of the invention, the data storage device may have a multiplicity of data storages that are attached along the length of the at least one sample chamber. A hanging chain of data storages may be formed on the sample chambers. Advantages, in particular for a sample withdrawal in sections, each in combination with a data storage, may result.

According to the invention, the cross section of the at least one sample chamber may vary along its length, so that at least one sub-chamber with a cross-sectional area that is larger than the cross-sectional dimensions of the inlet and outlet openings is formed. The sub-chamber(s) form pockets that advantageously hold a larger amount of sample and simplify a sample withdrawal in sections.

If the sample chambers consist of a flexible material, they may be connected with one another at their exterior walls, so that an integral, flexible sample chamber block is formed. The storage density during cryopreservation may thereby be increased.

The functionality of the cryostorage device according to the invention may further be increased, when a labeling device that comprises a labeling layer on the data storage device and/or labeling elements on the sample receptacle device, and/or at least one sensor, in particular a temperature sensor, and/or cooling surfaces on the sample chambers are provided.

A subject of the invention is also a method for the cryostorage of suspension samples, wherein these, as a result of capillary or exterior pressure forces, are taken up by at least one elongated sample chamber and are transferred into a cryo-preserved state therein. The cryostorage according to the invention generally occurs at a temperature below room temperature, at which a vitality-maintaining, continuous storing of the samples is possible. The selected temperature and the storing duration are chosen depending upon the application. The invention is particularly advantageously realizable with low-temperature storing at temperatures below minus 100° Celsius, and in particular at the temperature of liquid nitrogen.

Other advantages and details of the invention will become apparent from the following description of the attached drawings. In the figures,

DETAILED DESCRIPTION OF THE PREFERRED EMBODIMENTS

Figure 1:
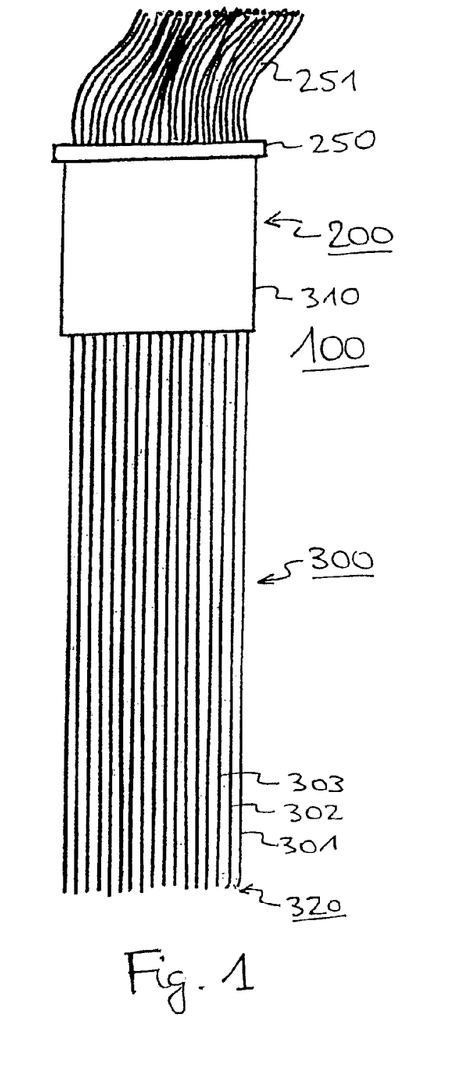
FIGS. 1 to 4: show different embodiments of cryostorage devices according to the invention.

FIG. 1 shows a first embodiment of a cryostorage device according to the invention 100 in a schematic side view. The cryostorage device 100 comprises a data storage device 200 and a sample receptacle device 300. The data storage device 200 comprises at least one data storage 210 that is located in a housing 310. The data storage 210 has an interface for the at least temporary intake of a plug connection 250 with electrical interconnections 251, through which the data storage 210 can be connected to a control device (not shown).

A known memory chip is provided as data storage 210, in which, depending upon the application, any data may be electrically, magnetically, or optically stored. For example, so-called flash memory is used.

The sample receptacle device 300 is connected to the data storage device 200. The sample receptacle device 300 comprises a multiplicity of tubular sample chambers 301, 302, 303, etc. that are individually hanging directly attached to the housing of the data storage 210 in the embodiment shown. In FIG. 1, 17 sample chambers are exemplified. It is emphasized that the invention is also realizable with one individual, tubular sample chamber or with a different number of sample chambers (e.g. up to 100 or more). The sample chambers may further be attached to the data storage device 200 by means of an attachment device (see FIG. 7).

The sample chambers (e.g. 301) each comprise a tube or a flexible capillary with an inner diameter that is substantially smaller than the length of the sample chamber. The inner diameter is for example in the range of 5 µm to 4 mm. The length of the sample chambers is chosen, for example, in the range of 0.5 cm to 10 dm. The ratio of cross-sectional diameter and length of a sample chamber is preferably less than 1/10. The sample chambers may consist of any suitable inert material, e.g. plastic, silicon rubber, glass, or semi-conductor material. The wall material of the sample chambers may be liquid-tight or permeable, depending upon the desired requirements for the cryostorage. In particular, an ion-permeable material, as known from dialysis tubes, may be used. Additionally, sensors (e.g. temperature sensors) may be provided in the wall material of the sample chambers or on the surface thereof. The sample chambers may be formed with a diameter that is constant along their length and that corresponds to the diameter of the inlet and outlet end (or inlet and outlet openings). In modified embodiments of the invention, a variation of the inner diameter is provided along the length of the sample chambers (see FIG. 6). A variation of the length of the sample chambers that belong to a cryostorage device may also be provided (see FIG. 2). The free ends of the sample chambers 301, 302, etc. of the sample receptacle device 300 according to FIG. 1 form the inlet ends 320, via which loading of the sample chambers preferably occurs. With the opposite ends that form, depending upon the application, outlet ends or pressure compensation ends, the sample chambers are attached to the data storage device 200, the housing 310, or a pressure distributor. The pressure compensation ends may be supplied with low pressure individually or together, in order to transfer suspension samples into the sample chambers in the manner explained below.

A particular advantage of the invention results, if the sample chambers used consist of a flexible material. The sample chambers are dimensioned in such a way that the inlet ends 320 may be adjusted in any arrangement, in order to take up suspension samples from containers, reservoirs or the like. This is possible with sample chambers from both macroscopically elastic materials, such as plastics, polymers, or metals, and materials with a higher hardness, such as glass, semiconductors, in particular silicon, carbon, or ceramics.

Figure 11:
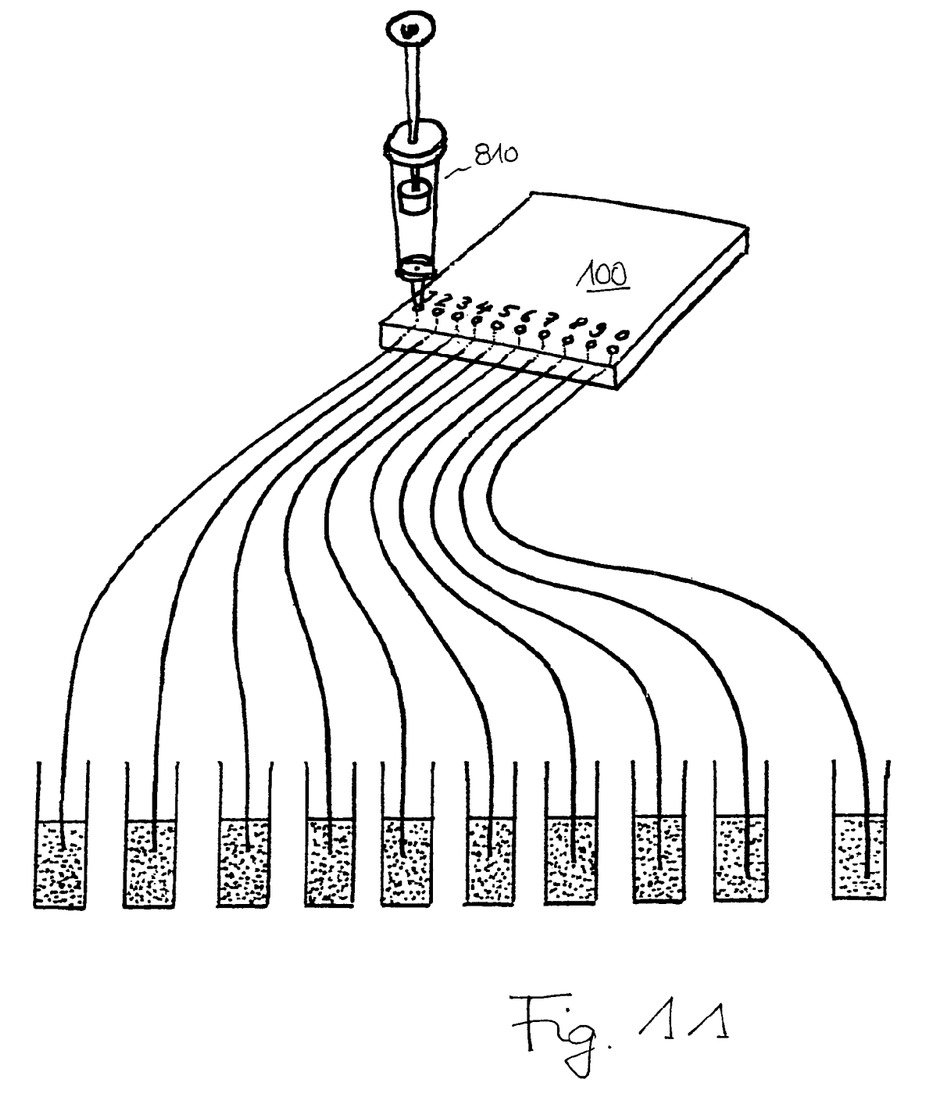

The use of a cryostorage device according to the invention, for example according to FIG. 1, occurs in accordance with the following steps (see also FIG. 11). First, loading of the sample receptacle device 300 occurs. Suspension samples are taken into the sample chambers from storage containers, e.g. the wells of a titer plate, by applying low pressure or as the result of capillary forces. Data for the characterization of the suspension samples taken up are written in the data storage device 200. In medical applications, for example, these data comprise identification data for the determination of the donor and the kinds of suspended cells, further characteristics of the donor, such as the blood type, optionally relevant literature data about the suspended cell types and already present measured data and/or image data, if any. Image data comprise for example light or electron microscopic images of suspended cells that serve the donor-specific characterization of the cells and later comparisons. Stored data are retrieved and/or added to during cryostorage. Lastly, the preservation step occurs. The cryostorage device with at least the sample receptacle device 300, however, preferably with both the sample receptacle device 300 and the data storage device 200, is transferred to an environment with reduced temperature. This environment exists for example in a cryo-container with liquid nitrogen or with gaseous nitrogen at T=−120° C. Further details of the cryostorage are explained below.

Figure 2:
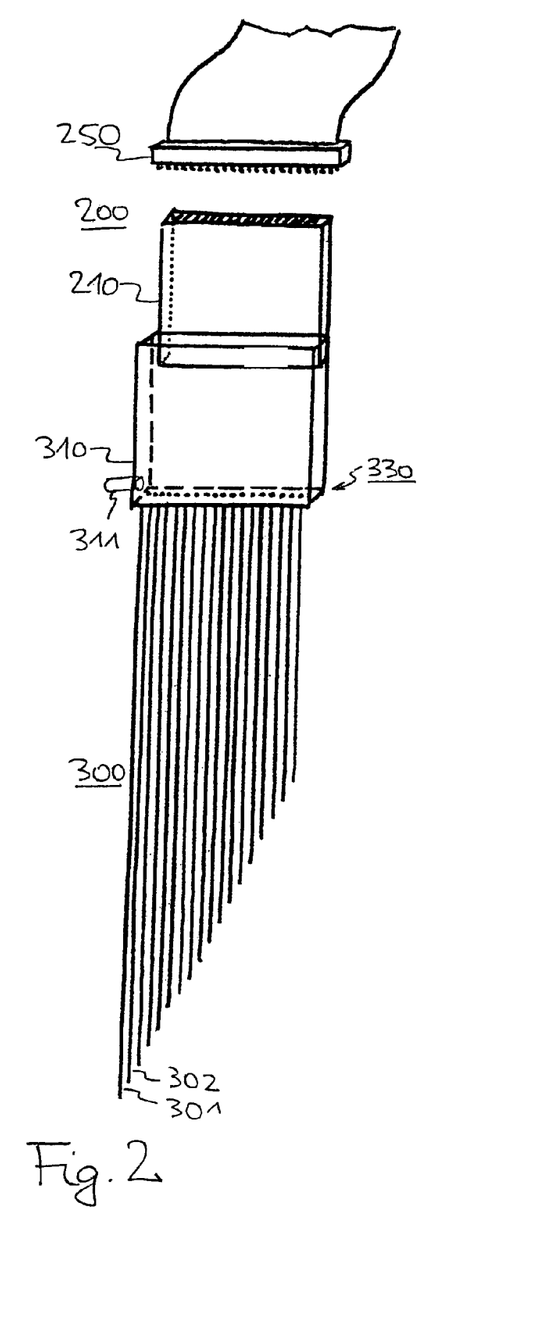

In the embodiment of the cryostorage device according to the invention illustrated in FIG. 2, the sample receptacle device 300 is formed by a series of tubular sample chambers 301, 302, etc., the length of which are different. For example, the length gradient shown is provided. This design has advantages during loading from suspension containers, in which, in consequence of a preceding centrifugation step, there is a cell type or especially cell size gradient. With the length gradient of the sample chambers, different cell types are taken into the individual sample chambers. The length gradient automatically provides a sorting by size.

FIG. 2 also shows further details of the housing 310 that forms an extension of the sample receptacle device 300. Housing 310 serves, on the one hand, the uptake of the memory chip 210 and, on the other hand, the provision of a working volume, via which a reduced pressure may be applied to the pressure compensation ends 330 of the sample chambers. For this, for example, a connection piece 311 for the build-up of the operating pressure is provided on housing 310. According to the invention, it is not mandatory that the housing 310 and the memory chip 210 are separate components. Alternatively, it is also possible that the sample chambers and optionally pressure transmission devices or the like are directly provided at or attached to the housing that is conditional on manufacturing, or the encapsulation of the memory chip 210.

Figure 3:
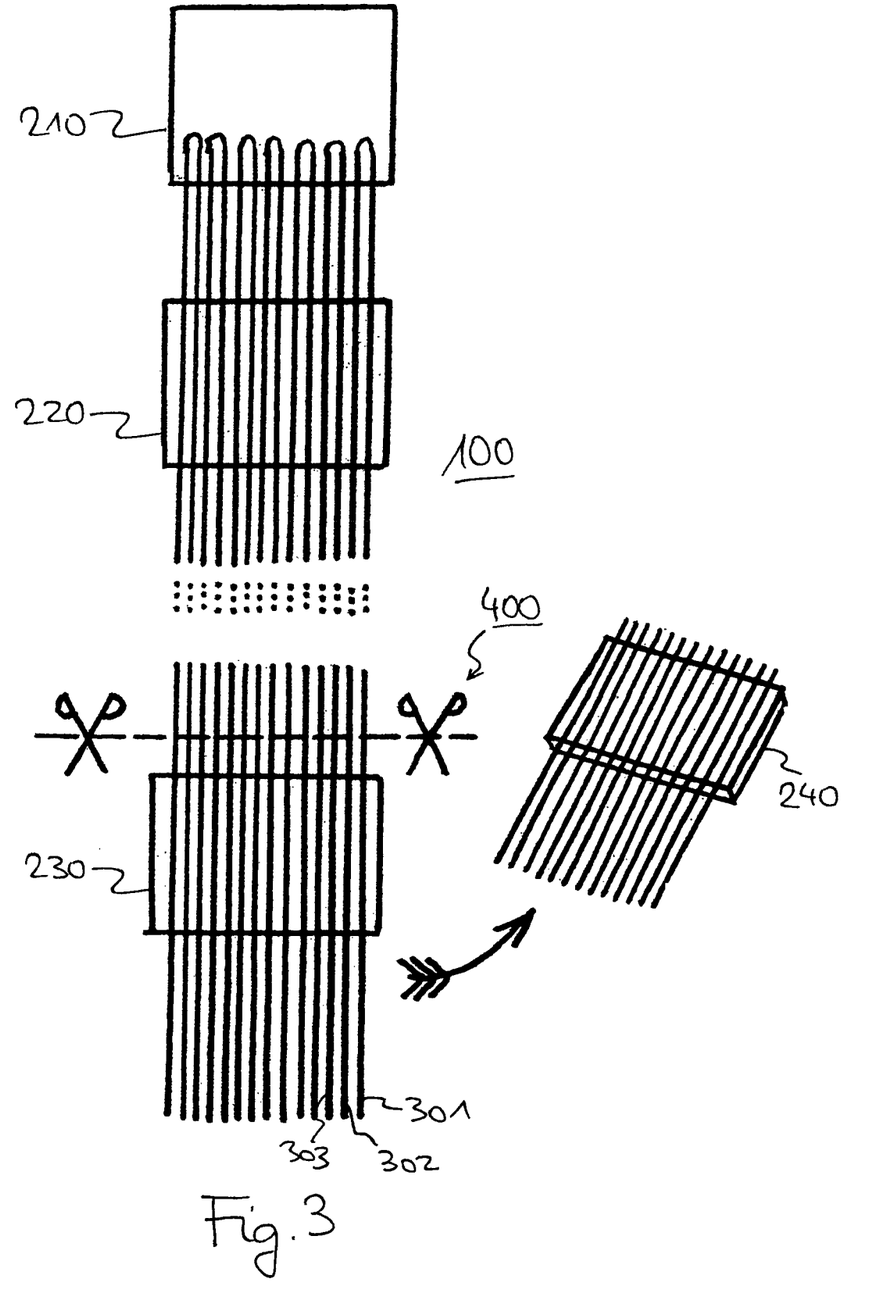

In accordance with FIG. 3, the data storage device 200 of a cryostorage device according to the invention 100 may also comprise a plurality of memory chips or data storages 210, 220, 230, 240, etc. The data storages are arranged along the length of the sample chambers 301, 302, etc. For example, a fixing of the sample chambers (e.g. gluing, molding or the like) on the encapsulation material of the data storages is provided. The advantage of this design is that parts of the cryo-stored samples may be taken up together with partial amounts of the stored data. This occurs for example with a schematically illustrated separating device 400, with the help of which the tubular sample chambers are separated according to a certain length with a respective data memory (e.g. 240). The separating device is preferably based on a mechanical separating operation (e.g. cutting, punching or the like) that is optionally combined with thermal treatment (e.g. local heating).

FIG. 3 also illustrates the possibility of a combination of sample chamber pairs. In the area of data storage 210, two adjacent sample chambers each are connected with one another, so that in pairs individual sample chambers 303 are formed. For loading, in each case, a free end (outlet end 330) of sample chamber 303 is supplied with reduced pressure while the other end (inlet end 320) extends into a reservoir with the sample suspension.

Figure 4:
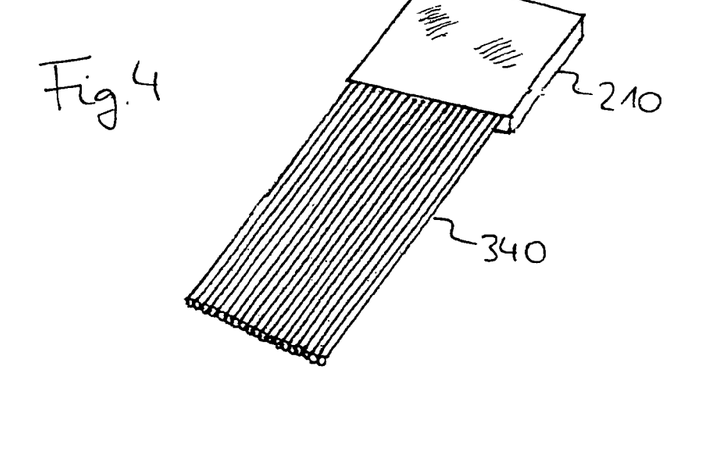

The sample chambers of the sample receptacle device 300 may, according to the invention, be formed as an integral sample chamber block (see FIG. 4) that is connected to the data storage device 200. Compared to the separate or free guidance of the sample chambers illustrated in FIG. 1, the sample chamber block 340 with sample chambers that are connected at their outer walls has the advantage of an increased stability both at room temperature and in the deep-frozen state. As with the seriation of wire connections to a flat cable, the sample chambers may be two-dimensionally arranged. Alternatively, a sample chamber block with a plurality of rows of sample chambers that are arranged on top of each other is usable. Alternatively, it is further possible to connect the sample chambers with one another as integral block in at least one first sub-area of the sample receptacle device 300, and to provide a separate arrangement, e.g. for flexible orientation of the inlet ends, in at least one second area.

Figure 5:
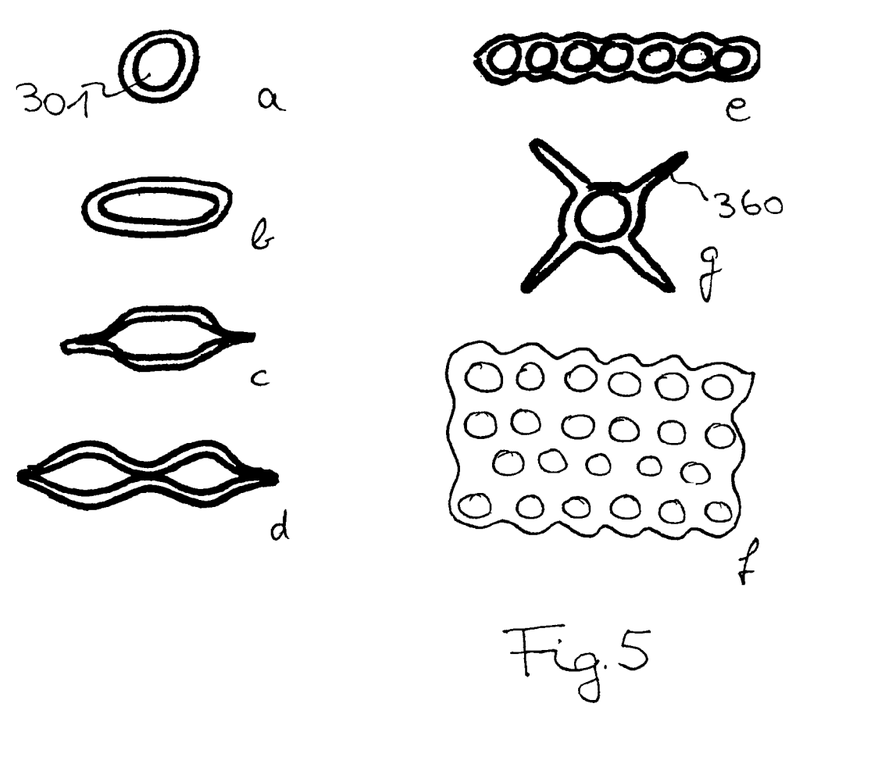
FIG. 5: shows schematic cross-sectional views of different embodiments of sample chambers used according to the invention.

A sample chamber used according to the invention generally has a tubular cross section. This means that the longitudinal dimension of the chamber is significantly larger than the average cross-sectional dimension of the sample chamber and particularly of the inlet and outlet openings. The internal shape of the sample chamber is thereby not limited to a specific geometry. In accordance with FIG. 5, the sample chamber 301 may have, for example, a circular (a) or oval (b) cross section. In case the sample chamber is formed by two sheet strips that are stitched together, the shape of the cross section may be in accordance with the partial pictures (c) or (d). More sample chambers may also be arranged as a row or side by side three-dimensionally (e, f). The partial picture (e), for example, corresponds to the embodiment of the invention illustrated in FIG. 4. In accordance with another embodiment of the invention (FIG. 5g), the sample receptacle device is provided with cooling elements 360. The cooling elements 360 are shaped for example as dents or projecting parts on the exterior of the sample chambers. This design has the particular advantage that the cooling process during transfer in the low-temperature state is accelerated.

Figure 6:
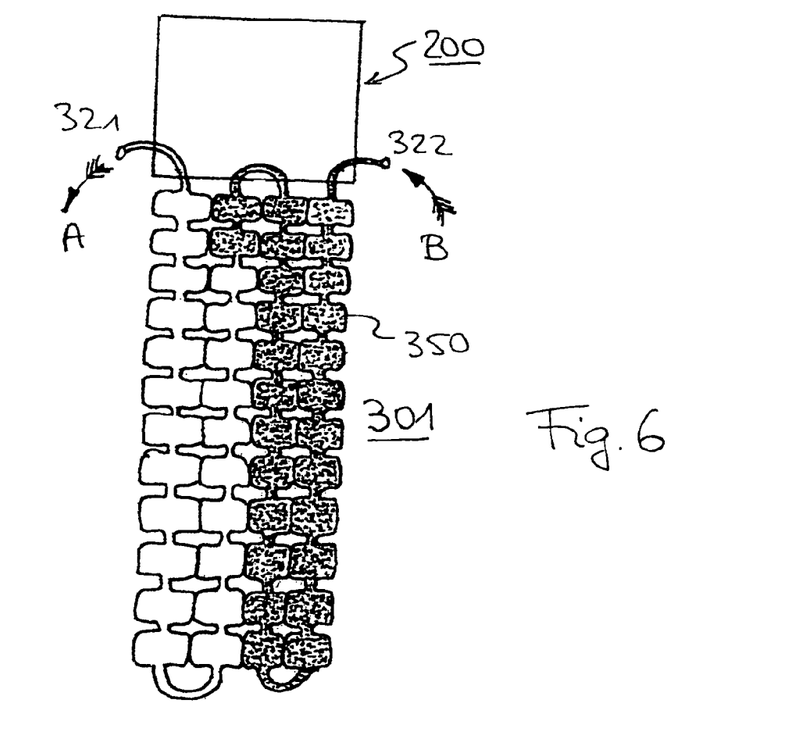
FIGS. 6 to 8: show further embodiments of cryostorage devices according to the invention.

According to the invention, the cross section of the at least one tubular sample chamber 301 may be variable along its length, as exemplified in FIG. 6. The design with a variable cross section has advantages with respect to handleability and functionality of the sample chambers. In accordance with FIG. 6, chamber sections with smaller cross-sectional dimensions and chamber sections with larger cross-sectional dimensions are formed. The chamber sections with the larger cross-sectional dimensions are also referred to as sub-chambers 350. In FIG. 6, an individual sample chamber 301 with a multiplicity of sub-chambers 350 is exemplified that is in a meander-shaped design attached to the data storage device 200. The loading of sample chamber 301 occurs by applying reduced pressure via outlet end 321 (arrow A), as a result of which a suspension sample (drawn dotted) is drawn into sample chamber 301 (arrow B) via inlet end 322. The advantage of this embodiment with variable cross section of the at least one sample chamber is the simplified handling of the cryostorage device according to the invention in the low-temperature state. Individual parts of the cryo-preserved suspension sample maybe removed without disturbing the remaining sample by mechanically separating the sub-chambers 340 from the sample receptacle device 300 by means of a suitable separating device. The chamber sections between the sub-chambers 340 thereby advantageously form predetermined breaking points for partial sample removal. At least one sub-chamber 350 is provided.

Figure 7:
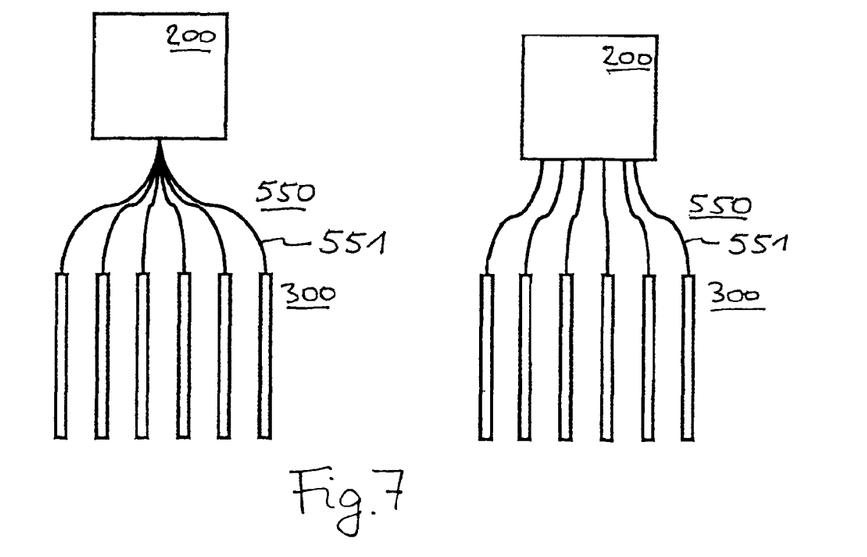

In accordance with FIG. 7, a cryostorage device according to the invention may be equipped with an attachment device 550 that serves the flexible, hanging attachment of sample receptacle device 300 to data storage device 200. The provision of a separate attachment device has advantages with respect to sample withdrawal, particularly in the cooled state. Partial samples in the form of individual sample chambers 301 may be easily withdrawn by cutting the corresponding parts of the attachment device 550, without the respective sample chamber being affected.

The attachment device 550 comprises a multiplicity of strips or bands 551, to each of which, on the one hand, a sample chamber 301 is attached and which, on the other hand, are attached to the data storage device 200. The strips 551 consist for example of a plastic band, at least one plastic fiber, a metal wire, or a metal band. The permanent connection between the sample receptacle device 300 and the data storage device 200 provided according to the invention is advantageously extended by the attachment device. The attachment of the strips 551 to the data storage device 200, e.g. the housing of a chip, may occur as a bundle (left partial picture) or separately (right partial picture).

In accordance with another embodiment of the cryostorage device according to the invention, the data storage device and/or the sample receptacle device may be provided with a labeling device. The labeling device comprises for example a labeling layer and/or labeling elements which preferably carry optically detectable or readable information. The provision of the labeling device schematically illustrated in FIG. 8 has the advantage that the handling of the cryostorage device, particularly within the operation of a cryo bank, is simplified. On the basis of the information recorded on the labeling device, a fast and reliable identification of a specific cryostorage device from a multiplicity of devices with the same set-up is possible. This is of advantage in all processes, in which a fast handling or manipulation of the cryostorage device is desired, such as during withdrawal from a cryo-medium.

Figure 8:
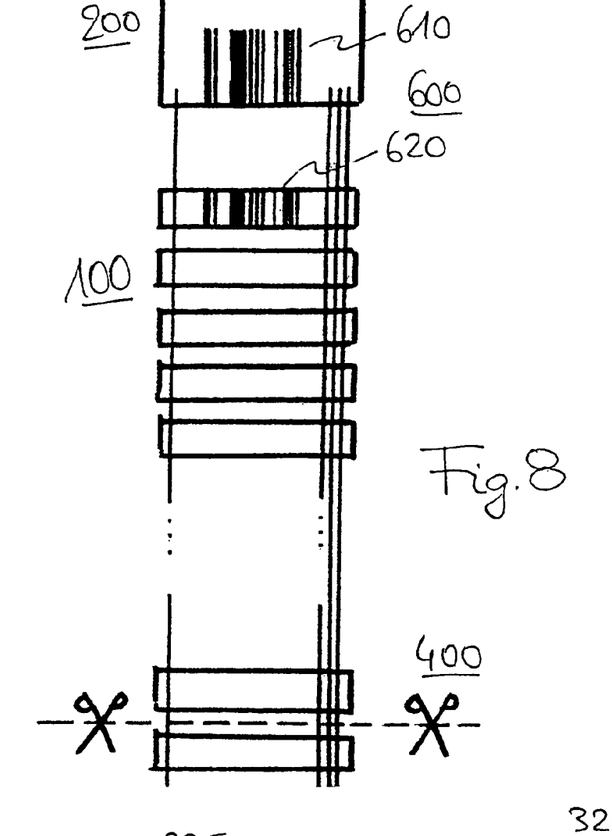

FIG. 8 shows as parts of the labeling device 600 a labeling layer 610 on the data storage device 200 and labeling elements 620 that are attached to the sample receptacle device 300. At least one labeling element that is attached to at least one tubular sample chamber is provided. Preferably, the illustrated arrangement, wherein a labeling element 620 each is attached to a multiplicity of sample chambers (partially shown), is realized. The labelings placed on the labeling layer 610 and the labeling elements 620 are formed, e.g., by a bar code which unambiguously identifies the cryostorage device and optionally contains further information about its making (e.g. first freeze or the like). The labeling contains on all parts of the labeling device 600 at least one identical partial information (e.g. identification) and optionally additional information, such as the position of a labeling element 620 along the length of the sample chambers 301.

The labeling layer 610 consists for example of an imprint on a housing of the data storage device 200. The labeling elements 620 are for example plastic strips that are attached to the at least one sample chamber. The sample chambers may be molded onto or adhesively bonded to the surface of the plastic strips, or can also be integrated in the bodies of the plastic strips. Each labeling is placed on the surface of the labeling elements 620 that is still free.

If a multiplicity of labeling elements 620 is provided, up-taking of partial samples may advantageously occur with retention of the assigned labeling information. A separation of sample chambers in combination with one or more labeling elements 620 may occur by means of the separating device 400.

According to the invention, the labeling elements 620 may be provided as parts of the stabilizing device 500 (see above). The labeling information may be placed on parts of the stabilizing device 500.

Figures 9, 10:
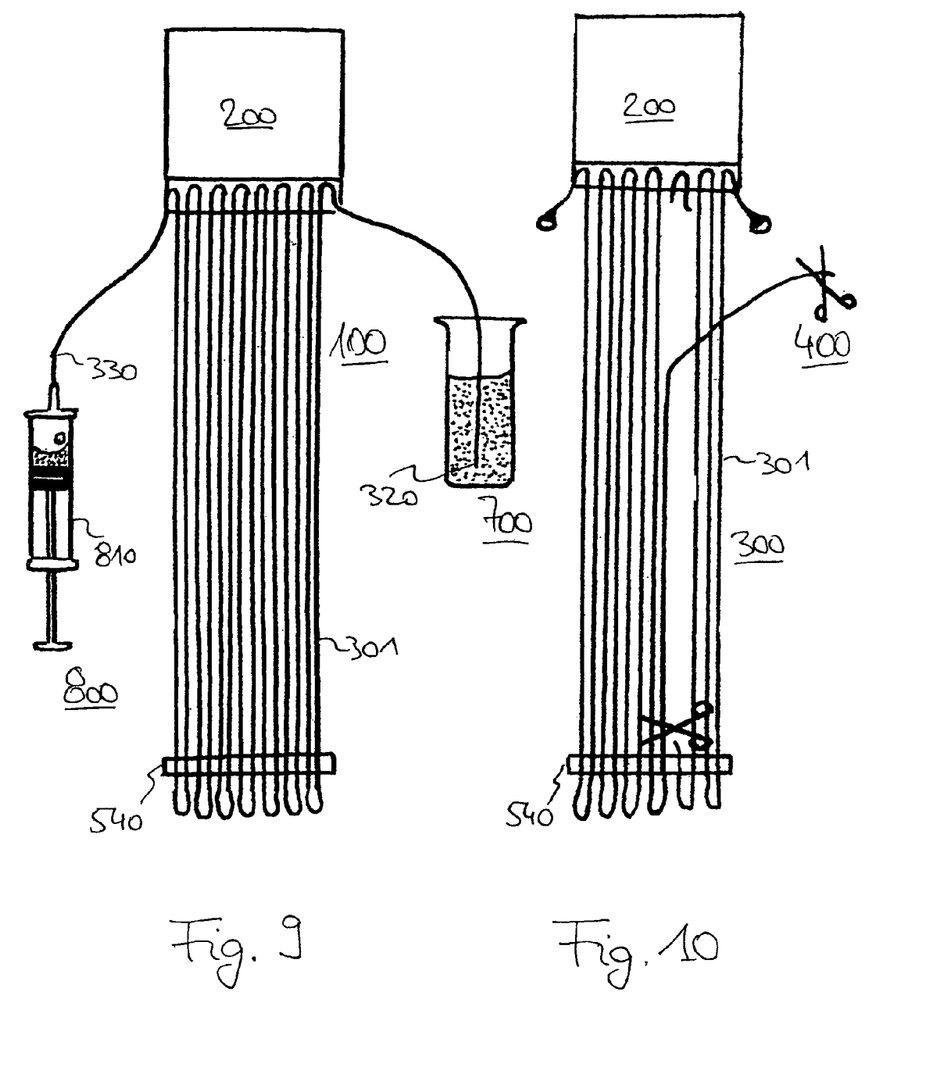
FIGS. 9 to 11: show illustrations for the handling of cryostorage devices according to the invention.

In FIG. 9, the loading of a cryostorage device according to the invention with a single sample chamber 301 that is designed in a meander shape is illustrated. A sample reservoir 700 with a single compartment, e.g. in the form of a beaker, centrifuge cup or the like, is provided. As a result of preceding processing steps, the suspension sample is present in the sample reservoir 700 with one or more types of cells, cell groups and/or cell components. The sample chamber 301 is dipped into the sample reservoir 700 with its inlet opening 320. At the opposite end 330, a suction device 800 that is formed, for example, by a liquid pipette, piston device, or syringe device 810 is provided. With operation of the suction device 800, the suspension sample may be sucked, advantageously free of bubbles, from sample reservoir 700 into sample chamber 301.

At the bottom end of the meander-shaped sample chamber 301, a stabilizing crosspiece 540 that serves as stabilizing device is depicted. During immersion of the sample receptacle device 300 in a cooling medium in particular, the loop ends of sample chamber 301 are held together. Hindering or interfering overlap with other sample chambers or sample chamber parts of other cryostorage devices that may be present in the cooling medium is avoided.

In FIG. 10, the withdrawal of a partial sample from the sample receptacle device 300 is illustrated. The withdrawal of a partial sample preferably occurs in the deep-frozen state, so that the remaining sample stays in the cryo-preserved state. A lengthwise segment is separated from sample chamber 301 by means of a separating device. Since the suspension density of the suspension sample is known in advance, the determination of the lengthwise segment may be chosen depending upon the number of the desired suspended particles that are to be contained in the withdrawn partial sample. Optionally, several lengths of the sample chamber 301 are withdrawn between the data storage device 200 and the stabilizing element 540.

In FIG. 11, the sequential loading of the sample chambers of a schematically illustrated cryostorage device 100 from a multiplicity of compartments 810, 820, etc. is illustrated. Each sample chamber, the position of which on the cryostorage device 100 is optionally identified by a number, is connected to a liquid pipette 810 in order to suck up one liquid sample each.

The withdrawal of samples from the cryostorage device according to the invention occurs, depending upon the application, in accordance with one of the following principles. Firstly, it is possible to thaw the entire cryostorage device and to withdraw the content of the at least one sample chamber. This occurs for example by applying a reduced pressure to one of the ends of the at least one sample chamber. Alternatively, it is possible to withdraw samples or partial samples in the deep-frozen state by mechanically separating (e.g. cutting) individual sample chambers or parts of sample chambers from the remaining cryostorage device by means of a separating device.

Figure 12:
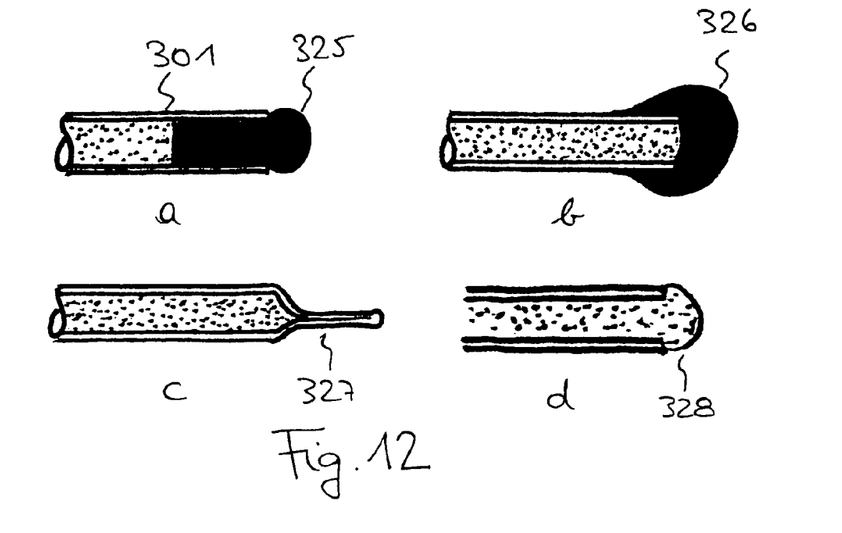
FIG. 12: shows enlarged partial views of the inlet and outlet ends of sample chambers.

In FIG. 12, different possibilities to seal the inlet and/or outlet ends of sample chambers 301 of cryostorage devices according to the invention are illustrated. A particular advantage of the tubular sample chambers used according to the invention is that the cross-sectional dimensions of the inlet or outlet openings are much smaller than the longitudinal dimensions of the sample chambers. Thereby, the area in which the sample that is to be preserved may be in contact with the environment (in particular with microorganisms), and thereby the risk of contamination, is minimized. Since a contamination in the low-temperature state by mass transfer is largely excluded, the sealing of the ends serves in particular a separation of the sample after loading of the sample receptacle device or after thawing. In accordance with the partial pictures (a) and (b), a stopper 325 or a cap 326 is used to close the sample chamber 301, which form a sealing. The sealing device consists here for example of wax or another plastic material. Alternatively, in accordance with the partial pictures (c) and (d), a seal may result from handling sample chamber 301 during withdrawal of partial samples. With tubular sample chambers, for example, a clamping point 327 may be formed, at which the opposed interior walls of sample chamber 301 adhere together after clamping and cutting of a partial sample. A separate clamping device may also be provided. In case the suspension sample is kept in sample chamber 301 as a result of capillary forces, the sample itself forms a liquid seal 328 which, however, is subjected to contamination by the environment.

The features of the invention that are disclosed in the foregoing description, the claims and the drawings may be of importance for the realization of the invention in its various embodiments both individually and in any combination.

The invention claimed is:

1. A cryostorage device comprising:
   at least one data storage device including at least one data storage adapted to store a plurality of data, and
   at least one sample receptacle device with at a plurality of sample chambers for the uptake of a suspension sample, the at least one sample chamber being directly attached to the at least one data storage device and having an elongated, hollow shape that extends from an inlet end over a predetermined length to an outlet end, the plurality of sample chambers having exterior walls being made of an inherently flexible and bendable material and being connected to each other along a portion of the sample chambers, the plurality of sample chambers being attached to the at least one data storage device in a flexible and movably hanging manner.

2. The cryostorage device according to claim 1, wherein the plurality of sample chambers is a hollow cylinder, a hollow cone, a pipe, a tube, or a hollow needle.

3. The cryostorage device according claim 1, wherein the plurality of sample chambers consists of a flexible, bendable material.

4. The cryostorage device according to claim 1, wherein the plurality of sample chambers is provided with at least one of a sensor, a temperature sensor, and cooling surfaces.

5. The cryostorage device according to claim 1, wherein the at least one data storage device comprises at least one data storage with a housing, the housing being connected with the at least one sample receptacle device.

6. The cryostorage device according to claim 5, wherein the at least one data storage device comprises a multiplicity of data storages that are attached along the length of the plurality of sample chambers.

7. The cryostorage device according to claim 1, wherein a cross-sectional dimension of the at plurality of sample chambers varies along a length of the plurality of sample chambers, so that at least one sub-chamber with a cross-sectional dimension that is larger than cross-sectional dimensions of the inlet and outlet openings is provided.

8. The cryostorage device according to claim 1, wherein the at least one sample receptacle device comprises a plurality of sample chambers connected with one another at their exterior walls, so that an integral, flexible sample chamber block is provided.

9. The cryostorage device according to claim 1, wherein a labeling device is provided that comprises at least one of a labeling layer on the at least one data storage device and labeling elements placed on the at least one sample receptacle device.

10. The cryostorage device according to claim 1, wherein an attachment device is provided, with which the plurality of sample chambers is attached to the at least one data storage device.

11. The cryostorage device according to claim 10, wherein the attachment device comprises strips arranged individually or as a bundle, each of the strips having a first and a second end with a sample chamber attached to the first end and the at least one data storage device attached to the second end.

12. The cryostorage device according to claim 1, wherein the at least one data storage is at least one data memory chip.

13. The cryostorage device according to claim 1, wherein the plurality of data includes a plurality of data bits.

14. A method for storing at least one suspension sample in a low-temperature state, comprising the steps of: uptaking the at least one suspension sample in plurality of sample chambers of a cryostorage device, the cryostorage device having at least one data storage device including at least one data storage adapted to store a plurality of data, and at least one sample receptacle device with a plurality of sample chambers for the uptake of a suspension sample, the plurality of sample chambers being directly attached to the at least one data storage device and having an elongated, hollow shape that extends from an inlet end over a predetermined length to an outlet end, the plurality of sample chambers having exterior walls being made of an inherently flexible and bendable material and being connected to each other along a portion of the sample chambers, the plurality of sample chambers being attached to the at least one data storage device in a flexible and movably hanging manner; and transferring the at least one suspension sample into a low-temperature state by positioning at least a part of the cryostorage device in a cryo-medium.

15. The method according to claim 14, wherein the uptaking comprises dipping the plurality of sample chambers with an inlet end in a sample reservoir and transferring of the suspension sample as a result of a reduced pressure applied at a corresponding outlet end or of capillary forces.

16. The method according to claim 14, wherein data that comprise the identification of the at least one suspension sample, measured data that were obtained from the suspension sample, reference data of reference samples, and behavior data about properties of the suspension sample during storage in the low-temperature state are stored in the at least one data storage device.

17. The method according to claim 14, wherein at least one partial sample is detached from the plurality of sample chambers in the low-temperature state by mechanical separation.

18. The method according to claim 17, wherein during the mechanical separation a local heating of the respective sample chamber in a vicinity of the at least one partial sample that is to be separated or a separation at an attachment device between the respective sample chamber and the data storage device occurs.

19. The method according to claim 14, wherein at least one of the inlet and outlet ends of the plurality of sample chambers is sealed by clamping, plugging, sealing, or a part of the at least one suspension sample.

20. The method according to claim 14, wherein the step of transferring the at least one suspension sample into a low-temperature state includes arranging the cryostorage device in an environment with a reduced temperature of less than −100° Celsius.

21. The method according to claim 14, wherein the step of transferring the at least one suspension sample into a low-temperature state includes arranging both the at least one data storage device and the at least one sample receptacle device in an environment with a reduced temperature of below −100° C.

22. The method according to claim 14, wherein the at least one data storage is at least one data memory chip.

23. The method according to claim 14, wherein the plurality of data includes a plurality of data bits.

24. A cryostorage device comprising:
at least one data storage device including at least one data storage adapted to store a plurality of data; and at least one sample receptacle device with plurality of sample chambers for the uptake of a suspension sample, the at least one sample chamber being directly attached to the at least one data storage device and having an elongated, hollow shape that extends from an inlet end over a predetermined length to an outlet end, both the at least one sample receptacle device and the data storage device being adapted to be transferred to an environment with reduced temperature below minus 100° Celsius, the plurality of sample chambers having exterior walls being made of an inherently flexible and bendable material and being connected to each other along a portion of the sample chambers, the plurality of sample chambers being attached to the at least one data storage device in a flexible and movably hanging manner.

25. The cryostorage device according to claim 24, wherein the at least one data storage is at least one data memory chip.

26. The cryostorage device according to claim 24, wherein the plurality of data includes a plurality of data bits.

* * * * *